United States Patent [19]
Bell

[11] Patent Number: 5,679,309
[45] Date of Patent: Oct. 21, 1997

[54] AUTOMATED RANDOM ACCESS ANALYZER

[75] Inventor: Michael Bell, Fullerton, Calif.

[73] Assignee: Beckman Instruments, Inc., Fullerton, Calif.

[21] Appl. No.: 572,094

[22] Filed: Dec. 14, 1995

[51] Int. Cl.⁶ .................................................. G01N 35/02
[52] U.S. Cl. .................... 422/67; 422/63; 422/64; 422/100; 436/43; 436/47; 436/49; 436/50; 436/180
[58] Field of Search ............................ 422/63, 64, 67, 422/100, 68.1; 436/43, 47, 48, 49, 50, 55, 164, 174, 179, 180; 364/497, 500

[56] References Cited

U.S. PATENT DOCUMENTS

| | | | |
|---|---|---|---|
| 4,091,089 | 5/1978 | Chichibu et al. | 424/12 |
| 4,157,871 | 6/1979 | Anderson et al. | 356/341 |
| 4,204,837 | 5/1980 | Sternberg et al. | 23/230 B |
| 4,276,258 | 6/1981 | Ginsberg et al. | 422/64 |
| 4,766,078 | 8/1988 | Gang | 435/291 |
| 4,906,433 | 3/1990 | Minekane | 422/64 |
| 4,908,186 | 3/1990 | Sakamaki | 422/64 |
| 4,908,320 | 3/1990 | Zakowski et al. | 436/45 |
| 5,037,612 | 8/1991 | Takahashi et al. | 422/64 |
| 5,051,238 | 9/1991 | Umetsu et al. | 422/64 |
| 5,104,808 | 4/1992 | Laska et al. | 436/48 |
| 5,171,695 | 12/1992 | Elkins | 436/501 |
| 5,183,638 | 2/1993 | Wakatake | 422/64 |
| 5,352,612 | 10/1994 | Huber et al. | 436/47 |
| 5,434,083 | 7/1995 | Mitsumaki et al. | 436/48 |
| 5,501,984 | 3/1996 | Hofstetter et al. | 436/518 |

FOREIGN PATENT DOCUMENTS

| | | |
|---|---|---|
| 0043079 A1 | 1/1982 | European Pat. Off. . |
| 0316766 A2 | 5/1989 | European Pat. Off. . |
| 0355823 A2 | 2/1990 | European Pat. Off. . |
| 0409126 A2 | 1/1991 | European Pat. Off. . |

OTHER PUBLICATIONS

Chapter 13, *Antibody–Antigen Reactions*, UCLA BIOMED.ILL, Feb. 17, 1994, pp. 249–275.

Hudson, Leslie et al., *Practical Immunology*, 2nd Ed., 1976, 1980, Blackwell Scientific Publications, pp. 94–112.

*Primary Examiner*—Long V. Le
*Attorney, Agent, or Firm*—William H. May; Gary T. Hampson; Margaret A. Kivinski

[57] ABSTRACT

An improved automated diagnostic analyzer and method of the type which includes a reaction carousel having cuvettes to receive sample and reactant for photometric analysis and to index and park for addition of sample, reactant and washing of cuvettes. Alternative reactant and/or sample addition points are provided so the analyzer controller may index cuvettes to provide greater frequency at which washing of cuvettes may take place simultaneously with addition of sample or reactant.

14 Claims, 5 Drawing Sheets

AUTOMATED RANDOM ACCESS ANALYZER

BACKGROUND

The present invention relates to automated diagnostic equipment and more particularly to automated in vitro analyzers.

Existing automated diagnostic analyzer devices are used to analyze a plurality of samples such as, for example, blood samples for immunonephelometric and/or turbidity analysis.

One type of automated analyzer runs one type of analysis upon many samples. These analyzers include an analysis wheel having circumferentially spaced cuvettes each adapted to be processed to receive a reactant and a sample, which react, and to analyze the reaction over time. After the reaction is complete the cuvette is processed to a wash cycle to be washed in preparation to receive a new charge of reactant and sample for analysis. In operation the analysis wheel is operated to spin, for photometric analysis of the reaction taking place in the cuvette, and to index, stop and park at a predetermined position and to thereafter spin again seriatim. Spaced reactant and sample addition points are provided to transfer an amount of a designated reactant and sample to a designated cuvette for analysis when the wheel is appropriately indexed and during the park cycle.

These analyzers, where the assays and the processing are the same or similar, operate in a sequence of progressive indexing of the cuvettes at each stop. That is, at each stop the parked position of a particular cuvette moves one relative position counter clockwise (or clockwise) from its position at the previous stop. As can be appreciated, each cuvette migrates counter clockwise (or clockwise) as the wheel spins, indexes and stops and parks. In this fashion, each cuvette passes the reactant and sample addition points. At the addition points reactants and samples are added to the cuvette at a predetermined time based upon the spin and park cycles and the number of cuvettes. Cuvettes in which the reaction is complete are emptied and washed, also at a time determined by the spin and park cycles and the number of cuvettes, i.e., the time necessary for the reaction complete cuvette to migrate to the wash station. After washing, each cuvette is ready to receive a new charge of reactant and sample. In progressive indexing machines, the cuvettes march as the carousel spins and indexes, to reach the wash point at the appropriate time for the wash cycle, i.e. at the completion of the reaction.

Reaction complete cuvettes are, at the wash cycle, emptied and washed to receive a new charge of the reactant and sample. In one analyzer such as a CX® 4CE or CX® 7 analyzers sold by Beckman Instruments of Brea, Calif. (CX® is a registered trademark of Beckman Instruments) there is a wash point which includes three pairs of probes, each pair adapted to register with adjacent cuvette pairs on the analysis carousel. As the cuvettes progressively index, their cycles are complete upon reaching the wash point. At the wash point, adjacent cuvette pairs are, in sequence, emptied and filled with a wash solution, indexed to be positioned under the next probe pair where the wash solution is emptied and filled with de-ionized water. Finally the cuvette pair is indexed to the last wash probe pair which empties and wipes the inside of the cuvettes, completing the wash cycle for the cuvette pair.

The number of analyses which can be processed for a given time, also known as throughput, in progressive analyzers is dictated by the number of cuvettes and the timing of the spin and park cycles. The time from the first introduction of reactant through introduction of the sample, through reaction and wash and return to position to receive a new charge of reactant is pre-set based upon the number of cuvettes and the spin and park cycles.

Another type of analyzer is a random access analyzer. These analyzers are somewhat similar to progressive analyzers; however, they are adapted to run any one or several assays upon many samples in randomly selected cuvettes. From a menu, the technician selects the different analyses to be run on each identified sample. The menu may include, for particular samples, haptoglobin, transferrin, C-reactive protein, rheumatoid factor and other assays.

After the random access analyzer has been programmed, it operates on an automated basis to run the designated analyses on each sample. In operation the analyzer operates on the spin and park cycles described above. However, each cuvette is processed, in a pre-programmed fashion, to receive the designated reactant(s) and sample, retain them during their reaction and, after the required reaction time has elapsed, wash the cuvette.

Depending upon the tests being run and any additional processing of the cuvettes as called for by the analysis protocol and further based upon the nature in which cuvettes are selected, it can be understood that adjacent cuvettes may have different processing times. Accordingly, and where adjacent cuvettes do have different processing times, using a pair wash technique of existing progressive analyses would require preserving a processed cuvette (i.e., the cuvette with the shorter processing time) until its neighbor has completed its processing. This preservation of processed cuvettes affects throughput since the processed cuvettes are unavailable to process other samples for analysis.

Accordingly, random access analyzers are typically provided with a single cuvette wash point. Being only able to wash a single cuvette at a time, the random access analyzer processor must recognize reaction complete cuvettes and designate them for wash. If a wash designated cuvette registers with the wash point while another cuvette designated for reactant or sample addition registers with the appropriate point during the same park cycle, the system opportunistically washes the reacted cuvette simultaneously with the addition of reactant or sample. Where opportunistic washing does not occur, washing of the reacted cuvette must wait for later opportunistic or a dedicated wash cycle occurs.

While the opportunistic washing of reacted cuvettes described above can be advantageous, such opportunistic washing of these types of analyzers can occur too infrequently to significantly increase throughput. The requirement for dedicated wash cycles or waiting for opportunistic washing decreases the throughput of the machine since wash designated cuvettes are preserved and since dedicated wash cycles require allocated time which therefore is not available to add reactant or sample. Addition of other wash points would affect the complexity and cost of the machine.

There is, therefore, a need for an analyzer and method which increases the throughput for random access analyzers without the addition of components such as additional wash stations.

SUMMARY

Toward this end the present invention is directed toward an automated, random access, clinical analyzer which increases the frequency for opportunistic washing of cuvettes. The greater the frequency of opportunistic washing, the less dedicated wash cycles required which, in turn, increases the throughput for the analyzer.

Accordingly, the analyzer and method according to the present invention include a rotatable, circular reaction carousel which has circumferentially spaced cuvettes. Each cuvette, according to the menu of the analyzer, is designated to receive a selected reactant and a selected sample for reaction and analysis and, post-analysis, be washed for re-use. As used herein a reactant is meant to also include buffers, diluent or other products to bring about the desired reaction. Any suitable number of cuvettes may be used such as, for example 40. A drive indexes the reaction carousel to position the cuvettes according to the menu and in proper sequence, for receipt of reactant, sample and for wash and for analysis. Specifically, where photometric analysis is used, the drive operates on a sequence of a spin cycle, during which the reaction carousel is spun for photometric analysis of reacting cuvettes, and to index and pause rotation, i.e. a park cycle, for a period of time for insertion of reactant, sample and/or for wash. As but an example, the analyzer can operate on a cycle of 2 second spin and 3 second park cycle for processing of the cuvettes.

Provided about the reaction carousel is a wash point having a single probe operated to engage, empty and wash a cuvette which is presented at the wash point during a park cycle. A reactant addition point, spaced from the wash point, includes a probe which is operated to transfer a reactant to a cuvette positioned thereat during a park cycle. Similarly a sample addition point has a probe which is operated to deposit a designated sample to a designated cuvette positioned at the sample point, also during a park cycle. Reactant and sample can also be added at a single reaction component addition station.

To increase throughput of the analyzer, at least a second reactant addition point is provided. Upon targeting a cuvette for reactant addition, the controller determines the first and second wash complements cuvettes. The first wash complement cuvette is the cuvette which would be positioned at the wash point when reactant is added at the first reactant addition point to the target cuvette. The second wash complement cuvette is the cuvette which would be positioned at the wash point when reactant is added at the second reactant addition point to the targeted cuvette. Once the wash complements are determined the controller compares the complements with the inventory of wash designated cuvettes. If the first wash complement is designated for wash, the controller indexes and parks the reaction carousel for reactant addition at the first addition point to the targeted cuvette while simultaneously and opportunistically washing of the first wash complement cuvette. If the first wash complement cuvette is not ready to be washed but the second wash complement cuvette is, the controller indexes and parks the reaction carousel for addition of reactant to the targeted cuvette at the second reactant addition point and simultaneously and opportunistically washing of the second wash complement cuvette. If neither of the first or second wash complement cuvettes are ready for wash, no washing occurs and the controller indexes and parks the targeted cuvette at the first reaction addition point and reactant is added.

The controller thereafter targets another cuvette for reactant addition, determines the wash complements and, if appropriate, opportunistically washes cuvettes while adding reactant.

As can be appreciated, providing addition to cuvettes at multiple points increases the frequency at which opportunistic washing can take place. The analyzer controller can opt between the determined wash complements to increase opportunistic washing.

To provide for multiple reactant addition points, the device and method according to the present invention includes a reactant transfer probe. The probe is controlled to transfer selected reactant at either of the first or second addition points. For this purpose the probe preferably pivots along an arc which brings it into registry with cuvettes parked at the first and second addition points.

Advantageously, the device and method according to the present invention can make a substantial contribution to system throughput without unnecessary addition of equipment such as more wash points, sample or reactant probes, piping or pumps necessary to service them. It has been found that providing a second reactant addition point and the concomitant determination of the wash complements can result in a 7–10% improvement in throughput, this improvement increasing where the menu of analyses calls for longer processing and analysis periods for the cuvettes.

In a further embodiment, multiple sample addition points may also be provided. The controller again determines wash complements and, in a fashion like to that described above, selects sample addition points to increase the frequency of opportunistic washing.

BRIEF DESCRIPTION OF THE DRAWINGS

These and other features and advantages will become appreciated with reference to the specification, claims and drawings wherein:

DESCRIPTION

Figure 1:
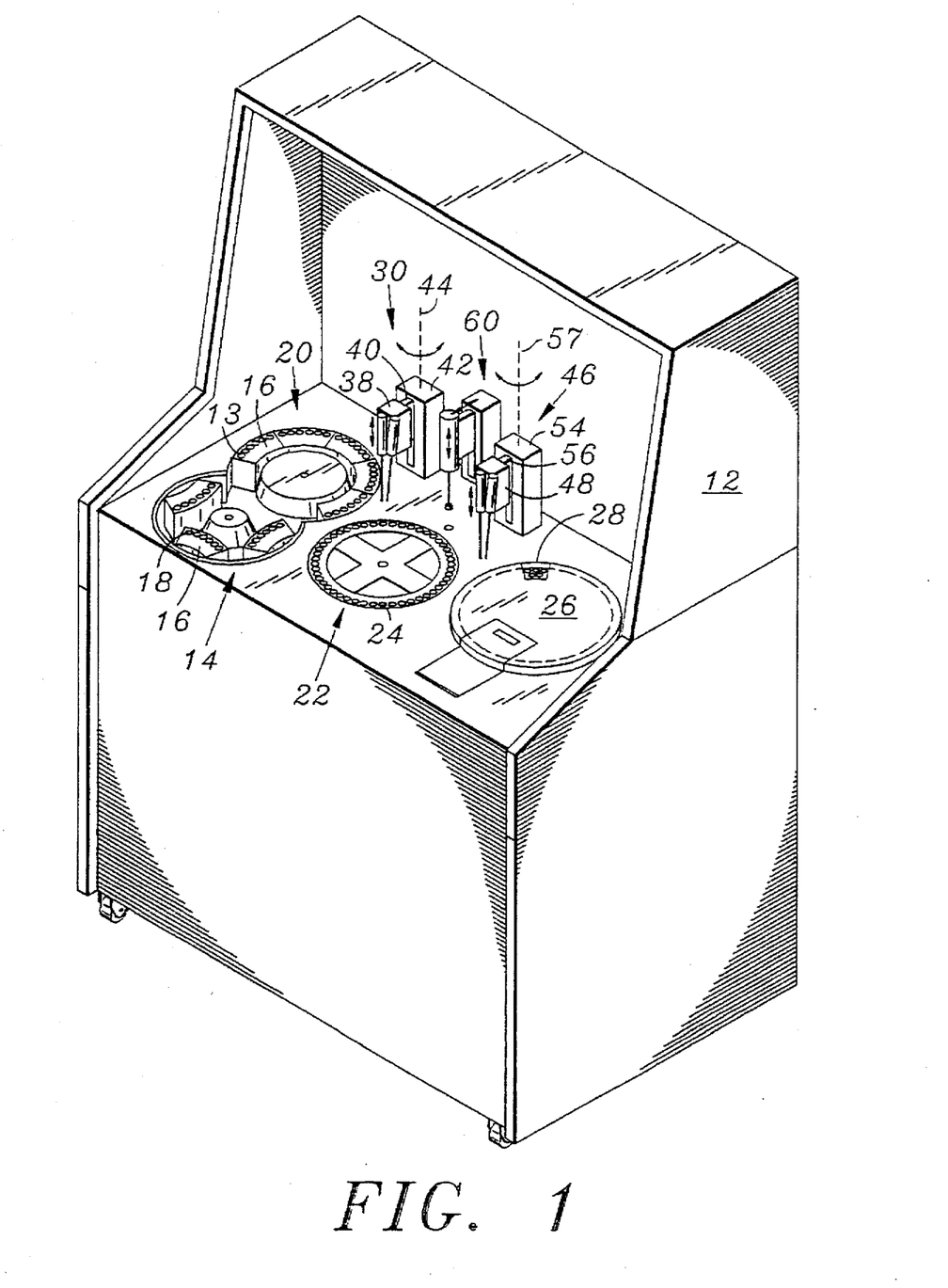
FIG. 1 is a perspective view of a random access analyzer incorporating the features of the present invention.
Figure 2:
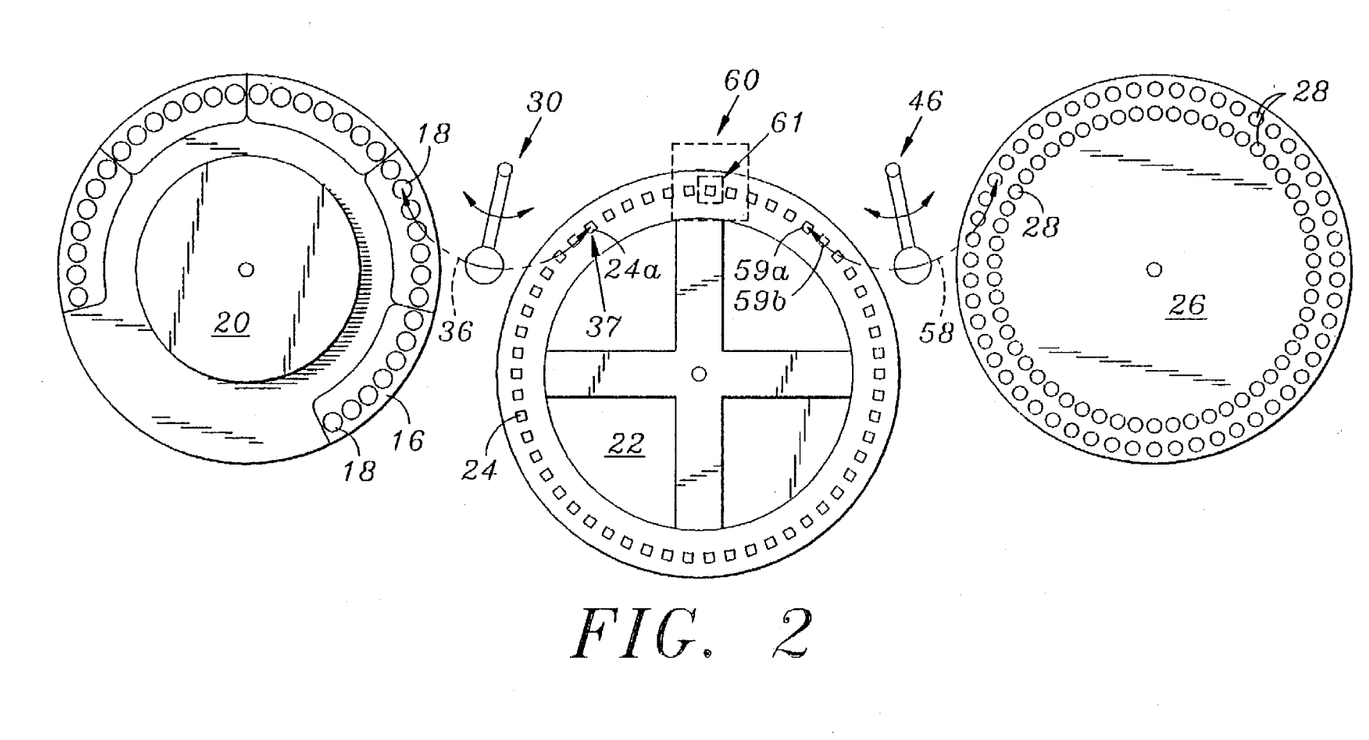
FIG. 2 is a top view of a portion of the analyzer of FIG. 1 illustrating the operation of the reactant, sample and wash stations according to the present invention.
Figure 3:
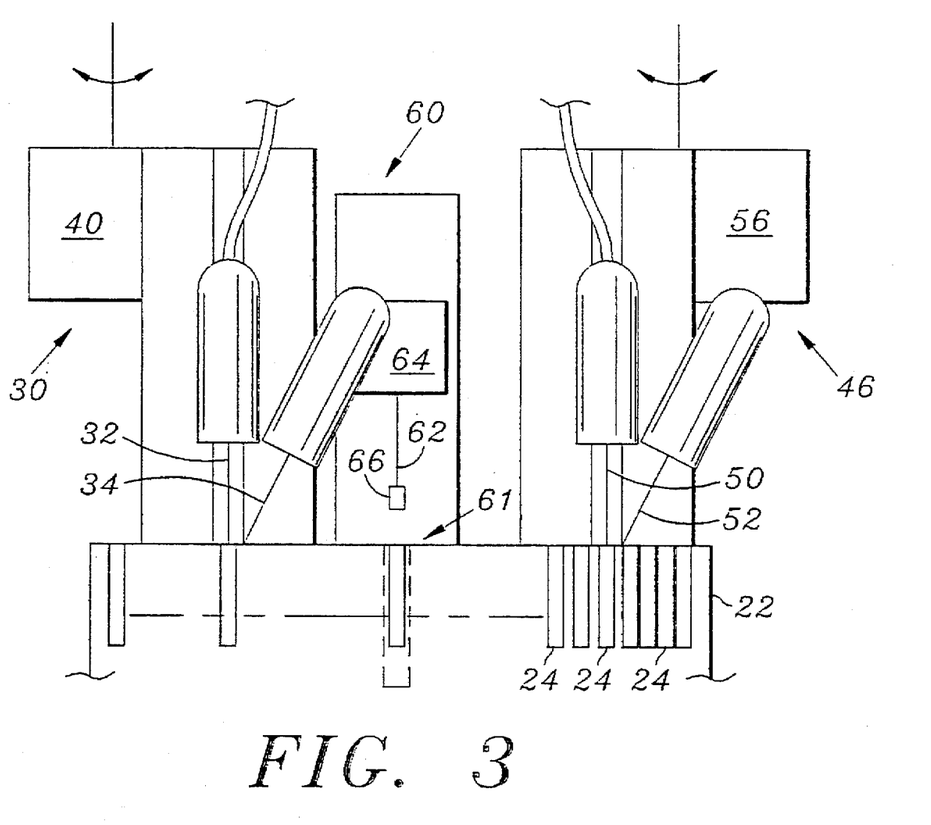
FIG. 3 is a partial end view of the analyzer of FIG. 1 illustrating the operation of the reactant, sample and wash stations according to the present invention.

Turning to the drawings, FIGS. 1–3 show an analyzer 10 incorporating the features of the present invention. The analyzer 10, as described below, is loaded with a plurality of samples and is adapted to run one or more assays on each of the samples selected from a menu. For example, in a clinical setting, the analyzer 10 may have a menu of assays including serum albumin, immunoglobulin A (IgA), immunoglobulin G (IgG), immunoglobulin M (IgM), prealbumin, haptoglobin, transferrin, C-reactive protein, $\alpha_1$-antitrypsin, $\beta_2$-microglobulin, or other tests. Once the samples have been loaded into the analyzer 10 and the system initiated, the specific assays are run on specific samples on an automated basis according to the selected assay sequence and the results provided.

The analyzer 10 includes a housing 12 adapted to house the various pumps, piping, drives and controllers to operate the equipment as hereinafter described. This equipment is generally as is provided in the Synchron CX System Analyzers such as CX®4CE/CX®7 provided by Beckman Instruments of Brea, Calif. the assignee herein and which are generally known. Therefore, the details of the equipment and operation will be omitted except where such description aids in the understanding of the invention.

The analyzer includes a processor (not shown) which controls the various operations and functions of the analyzer 10. Such a processor may be a Hewlett Packard Vecta with an 80 megabyte hard drive including a single high density 1.44 megabyte, 3.5 inch floppy drive. A data input device such as a keyboard and monitor (not shown) are also to provided for communication with the processor to program functions and select from the menu of analyses as hereinafter described. A printer (also not shown) provides a printout of data generated as a result of the analysis.

As with known random analyzers, the processor allows the operator to identify specific samples as loaded into the analyzer 10 and to select from a menu of assays the particular assays or assays to be conducted on each sample to be processed in a particular run of the analyzer 10. Not only may some of these assays have different processing times dictated by factors including the incubation period necessary to bring about the reaction for analysis, but some test sequences may require secondary processing. That is, after the initial reaction takes place, secondary addition of reactant may be required and the secondary reaction analyzed to complete the assay of the sample. Accordingly for any particular sample, and dependent upon the assay selected from the menu to be run on a particular sample and its assay sequence, the time necessary to process the cuvettes from additions of the reactant(s), sample, analysis, secondary additions (if required) and washing may vary from assay to assay.

To receive samples as loaded into the analyzer 10, the analyzer 10 includes a loading tray 14 which receives a plurality of sample sectors 16, each of the sectors 16, in turn, mounting a plurality of sample vials 18. As illustrated, the sample sectors 16 may mount seven such sample vials 18 which may include, for example, human blood samples from various patients for clinical analysis.

As is known in the art, each of the sample sectors is encoded, as by a stick-on bar code label (not shown), to enable a processor bar code reader (not shown) to identify the individual sectors 16 as well as the samples mounted thereon. A drive (not shown) indexes the loading tray 14, in a known fashion, and a transfer mechanism (also not shown) transfers the sample sectors 16 from the loading tray 14 to a sample wheel 20. The sample wheel 20 is also driven by a drive (not shown) which can rotate and index the sample wheel 20 to park a desired sample at a selected position. The encoding provided to the sample sectors 16 enables, through known means such as a bar code reader, the processor to identify the individual samples and their position on the sample wheel 20.

To receive a portion of a sample and reactants such as antigen, antibody, buffers, diluent or other products to bring about the desired reaction for analysis, the analyzer 10 also includes an analysis carousel 22 disposed adjacent to the sample wheel 20. The analysis carousel 22 has circumferentially disposed, re-usable cuvettes 24 which are each adapted to receive the various reactants and a sample and to retain them for the reaction and for analysis. As shown in FIGS. 2 and 3, the cuvettes 24 may each be rectangular in cross-section and, where analysis is through light absorption (turbidimetry) or light scattering (nephelometry), the cuvettes are themselves substantially transparent. Any number of cuvettes 24 may be disposed on the analysis carousel 22 such as, for example, 40 cuvettes 24 equally spaced circumferentially around the analysis carousel 22.

For purposes which will hereinafter become evident, the analysis carousel 22 is driven, in a known fashion, to rotate and index the cuvettes 24 to desired positions for processing samples. The analysis carousel 22 is encoded in a known fashion so that the processor may identify and determine the position of each cuvette 24 during processing. As with other types of analyzers, the analysis carousel 22 operates on a timed sequence which includes a spin cycle, during which the analysis carousel 22 is rotated for photometric analysis of the reaction taking place in the cuvettes 24, and a park cycle. While any suitable sequence may be appropriate, the analyzer 10 according to the present invention has an overall combined cycle rate of five seconds encompassing a two second spin cycle and a three second park cycle as well as acceleration and deceleration. It is during the two second spin cycle that the photometric analysis is made of the reactions taking place in the cuvettes 24 and during the three second park cycle that the cuvettes are parked for reactant and sample addition and are washed for re-use.

To provide an inventory of reactants selected to bring about the desired reaction for analysis, the analyzer 10, also as is known in the art, includes a reactant wheel 26. The reactant wheel 26, as shown in the drawings, includes a plurality of containers 28 arranged in concentric disposition each containing a reactant, diluent, buffer or other product (referred to herein collectively as reactant) known and used to bring about the assays of the menu. The various containers 28 and their position on the reactant wheel 26 are identified by the processor and the reactant wheel 26 is driven, in a known manner, to position the required reactant in position for transfer and add selected reactant to the cuvettes 24 at the analysis carousel 22 as described below. Typically the reactant wheel 26 and containers 28 are refrigerated.

While the foregoing description sets forth sample and reactant wheels 20, 26 it is to be understood that the inventory of samples or reactant or both may be dispersed on any suitable measurable, indexing platform such as a linearly moveably tray, belt or the like.

To transfer a selected sample to a selected cuvette 24, the analyzer 10 includes a sample transfer station 30 including thereon a hollow sample probe 32 and mixer 34. As illustrated in FIGS. 1–3, the sample station 30 is adapted to swing the sample probe 32 and companion mixer 34 to traverse a sample transfer arc 36 which intersects the sample wheel 20 and its vials 18 as well as at least one cuvette 24 positioned and parked at a sample addition point 37. For this purpose, and in a known fashion, the sample station 30 includes a sample probe elevator 38 mounting the sample probe 32 and mixer 34 for vertical displacement to insert the sample probe 32 and mixer 34 into the vials 18 and a cuvette 24 parked at the sample addition point 37. The sample probe elevator 38 is in turn mounted on an arm 40 coupling the sample probe elevator 38 to a pivot 42 controlled by the processor to pivot the arm 40 and sample probe elevator 38 about an axis 44 to swing the sample probe 32 and mixer 34 along the sample transfer arc 36 as described above.

In operation, the sample wheel 20 is disposed to register and park a designated sample vial 18, shown in FIG. 2 as vial 18*a*, at the sample station 30 for transfer. The sample station 30 is controlled by the processor to pivot and position the sample probe 32 over the vial 18*a* and the sample probe elevator 38 is controlled to lower the sample probe 32 into the vial 18*a*. The sample probe 32 aspirates a pre-determined portion of the sample into the probe 32 for transfer to a cuvette 24. Thereafter the elevator is raised and the sample station 30 pivoted along the sample transfer arc 36 to position the sample probe 32 in position to transfer the sample to a cuvette 24 parked at the sample addition point 37. In cooperation with the sample station 30, the analysis carousel 22 at the conclusion of a spin cycle stops and parks a designated cuvette, shown as cuvette 24*a*, at the sample addition point which lies along the sample transfer arc 36 for receipt of the sample. During the park cycle the sample probe 32 lowers and deposits the sample into the cuvette 24a, mixes and retracts. Thereafter, the sample probe 32 and mixer 34 are positioned and lowered into a wash cup where the components are washed, raised and re-positioned to transfer another sample.

The sample wheel 20, sample station 30 and analysis wheel 22 operate in this controlled fashion to transfer samples to designated cuvettes 24.

To transfer reactants from the reactant wheel 26 to designated cuvettes 24, the analyzer 10 also includes a reactant transfer station 46 as shown in FIGS. 1–3. The reactant transfer station 46 includes a reactant elevator 48 mounting thereon, for up and down motion, a hollow reactant probe 50 and a mixer 52. The reactant elevator 48 is coupled, like the sample transfer station 30, to a pivot 54 by an arm 56, the pivot 54 being driven and controlled by the processor to swing the arm 56 and reactant elevator 48, reactant probe 50 and mixer 52 about an axis 57 to traverse a reactant transfer arc 58 as shown in FIGS. 1 and 2. The reactant transfer arc 58 intersects the containers 28 arranged on the reactant carousel 26 as well as a pair of first and second reactant addition points 59a and 59b. While the drawings and the following description refers to the addition points 59a,b as registering with adjacent cuvettes, it is to be understood that, depending upon the arrangement of the analysis carousel 22, reactant wheel 26 and the radius of the reactant transfer arc 58, that the reactant addition points 59a,b need not be adjoining. The reactant addition points 59a,b may register with cuvettes 24 spaced apart by one or several intervening cuvettes 24.

In operation, and as required by the processing steps pre-programmed into the analyzer 10 and the analyses selected from the menu, the reactant wheel 26 is indexed to position a designated container 28 to intersect the reactant transfer arc 58. The reactant transfer station 46 is controlled to swing the reactant probe 50 to a position above the designated container 28. The reactant probe 50 is lowered by the reactant elevator 48 and a pre-determined amount of the reactant is aspirated into the reactant probe 50 in a known fashion. Thereafter the probe 50 is raised, pivoted about the reactant transfer arc 58 to the analysis carousel 22. During a park cycle, the reactant probe 50, for purposes which will hereinafter become evident, is controlled to deposit the reactant into cuvettes 24 positioned at one of the first or second reactant addition points 59a, 59b. In this fashion, reactant is transferred to designated cuvettes 24 as hereinafter described.

The analyzer 10 also includes a wash station 60 disposed about the perimeter of the analysis carousel 22. The wash station 60 includes a hollow wash probe 62 adapted to engage with cuvettes 24 which are indexed to a position and parked to register with the wash station 60 at a wash point 61. For this purpose the wash station 60 includes a wash station elevator 64 mounting the wash probe 62 as shown in FIGS. 1 and 3. The wash probe 62 includes at its end an appropriately configured, e.g. parallelpipedal, wiper 66 adapted to be closely received by cuvettes 24 to wipe the interior sidewalls thereof.

The wash station probe 62 is raised and lowered, in a known fashion to be received by a cuvette 24 parked at the wash point 61 to aspirate the contents of the processed sample from the cuvette 24, inject and thereafter aspirate a cleaning solution, inject and aspirate rinse solution and wipe the sidewalls of the cuvette 24 to clean the cuvette 24 for processing further samples. Thereafter the wash probe 62 is raised from the cuvette 24 and readied to engage subsequent cuvettes 24 which register and are parked at the wash point 61.

Initially, the analyzer processor, as with prior analyzers, is inputted with data identifying samples and designating the various analyses to be conducted on each sample to determine the scheduling for addition of reactants and samples (cycle scheduling) described below. The sample vials 18 are loaded into sectors 16 and the sectors are positioned in the sample tray 14. Reactant containers 28 are positioned on the reactant carousel and their positions and contents are imputed into the processor.

Figure 4:
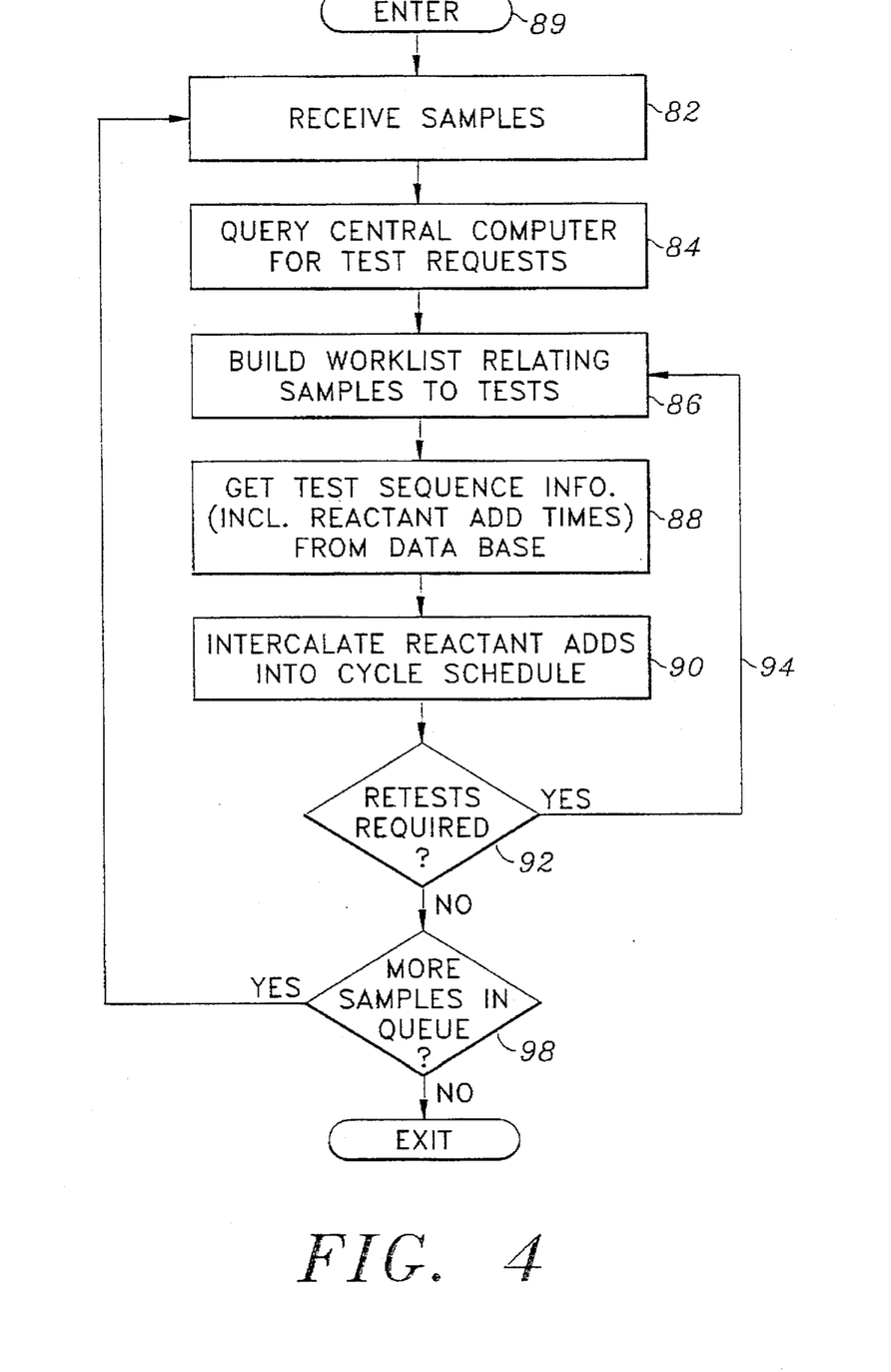
FIG. 4 is a flow chart illustrating scheduling for the analyzer.

The general cycle scheduling for the analyzer processor is illustrated in FIG. 4. After the processor is initiated at 80, samples are identified as they are received at 82 by the analyzer 10. The processor at 84 inquires of an interfaced central processor (not shown) which analyses are to be run on the individual samples. From the menu for each of the samples the processor at 86 builds a worklist comparing the samples with the analyses to be run on the samples. At this point at 88 the processor recalls from a stored data base the test sequences, including reactant addition times (which may include a warm-up time for chilled reactants to warm to a temperature compatible with sample addition and times between addition of additional or different reactants during processing of the analysis) and secondary processing. The processor intercalates reactant addition into the cycle schedule as at 90. As shown at 92, if retesting is required that too is accounted for in determining and building the worklist as shown by loop 94. If no retesting is required and all samples are received and identified, the cycle scheduling pre-processing is exited and the analyzer 10 is initiated to begin processing samples. Alternately if new samples are added either after initial pre-processing or during operation of the analyzer 10, the processor continuously prompts for additional samples to be identified and the analyses determined. As shown at 98, if additional samples remain to be pre-processed, the cycle scheduling is appropriately programmed to include those additional samples in building or updating the worklist and cycle schedule.

After inputting the appropriate information in the processor identifying the samples and the analyses to be run and the processor has built the worklist and determined cycle scheduling, processing is initiated. The sectors 16 are transferred to the sample carousel 20 and their positions are read and provided to the processor to identify the position of the individual samples. Thereafter the analysis carousel 22 begins its cycle of spinning for analysis and indexing to a parked positions. The processor is provided with input as by suitable encoding to determine the position of individual cuvettes 24.

If during operation additional samples are added to the queue of samples, the sample identifying information and tests and their sequences are inputted and cycle scheduling is updated to provide for the analyses on all samples.

To process a sample, reactant is added to a selected clean cuvette from the inventory of clean cuvettes on the analysis carousel 22. To transfer reactant, the required reactant is aspirated from the appropriate container(s) 28 into the reactant probe 52 at the reactant transfer station 46. After aspirating the appropriate reactants, the reactant probe 50 may be pivoted and lowered into a wash cup to wash any excess reactant from the outside of the probe. The probe 50 is thereafter raised and positioned over the analysis carousel 22. Thereafter the analysis carousel 22 stops in an indexed, parked position to park the selected empty, clean cuvette at either the first or second reactant addition points, as shown in FIG. 2, according to the processor determination as described below. The reactant probe 50 is positioned and lowered into the selected cuvette parked at either of the aforesaid positions. Once inserted in the cuvette the reactants are delivered from the reactant probe 50. Thereafter the analysis carousel 22 may be operated through multiple spin and park cycles for a predesignated period of time (during which reactant and sample can be added to other cuvettes 24) so that the reactants deposited in the selected cuvette may be brought from their refrigerated temperature, at which they are kept at the reactant carousel 26, to an appropriate reaction temperature. After an appropriate time has elapsed for temperature adjustment, the processor designates the selected cuvette as being ready to receive the companion sample, indexes and parks the selected cuvette 24 at the sample transfer station 30.

During the delivery of the reactants by the reactant transfer station 46 described above or during the various cycling of the analysis carousel 22 and prior to indexing and parking of the cuvette at the sample transfer station 30, the sample transfer station 30 can be controlled to, in the manner described above, aspirate an appropriate sample from a designated sample vial 18. As with reactants, after aspirating the appropriate sample amount from the sample vial 18, the sample probe 32 may be operated and lowered into a wash station to wash cup from the exterior of the probe 32. When the analysis carousel 22 has rotated and parked the selected cuvette at the sample transfer station 30, the probe 32 and mixer 34 are lowered into the cuvette and the sample is deposited and mixed with the reactant in the cuvette. Thereafter the probe 32 and mixer 34 are withdrawn and re-positioned at the wash cup for washing in anticipation of picking up a new sample.

The transfer of reactant and sample to the analysis carousel 22 takes place during the park cycles which, as described above, may be for a period of three seconds. Once the sample and reactant are mixed, the reaction for analysis begins taking place in the cuvette 24. During each spin cycle, the reaction is analyzed photometrically in a known fashion. The reaction may take place over a period of several minutes or longer and varies with respect to the type of analysis being run.

Due to the timing of the spin and park cycles, the reactant transfer station 46 and sample transfer station 30 are operated on different park cycles. That is, during any one park cycle reactant may be delivered to a designated cuvette 24. During the next subsequent park cycle, a sample is delivered to a cuvette 24 designated to receive the sample. Reactant and sample are not transferred during a single park cycle. In this fashion, the reactants and samples are brought together in designated cuvettes for analysis.

Some analysis may require late addition of reactants. For example, once a designated reactant and sample are brought together in a cuvette 24 and the reaction analyzed, it may be necessary to further process the cuvette by indexing it and parking it at the reactant transfer station for receipt of additional reactant. Due to the different incubation periods of the reactions taking place in the cuvettes and the requirement of some analyses to have late addition of reactant, it can be understood that many of the cuvettes 24 will finish their processing and analysis at different times. It is further to be understood that preserving cuvettes in which the sample has been processed and analyzed and which are wash-ready disadvantageously affects throughput in that these cuvettes 24 are not promptly washed and readied to receive a new charge of reactant and sample for analysis.

Figure 5:
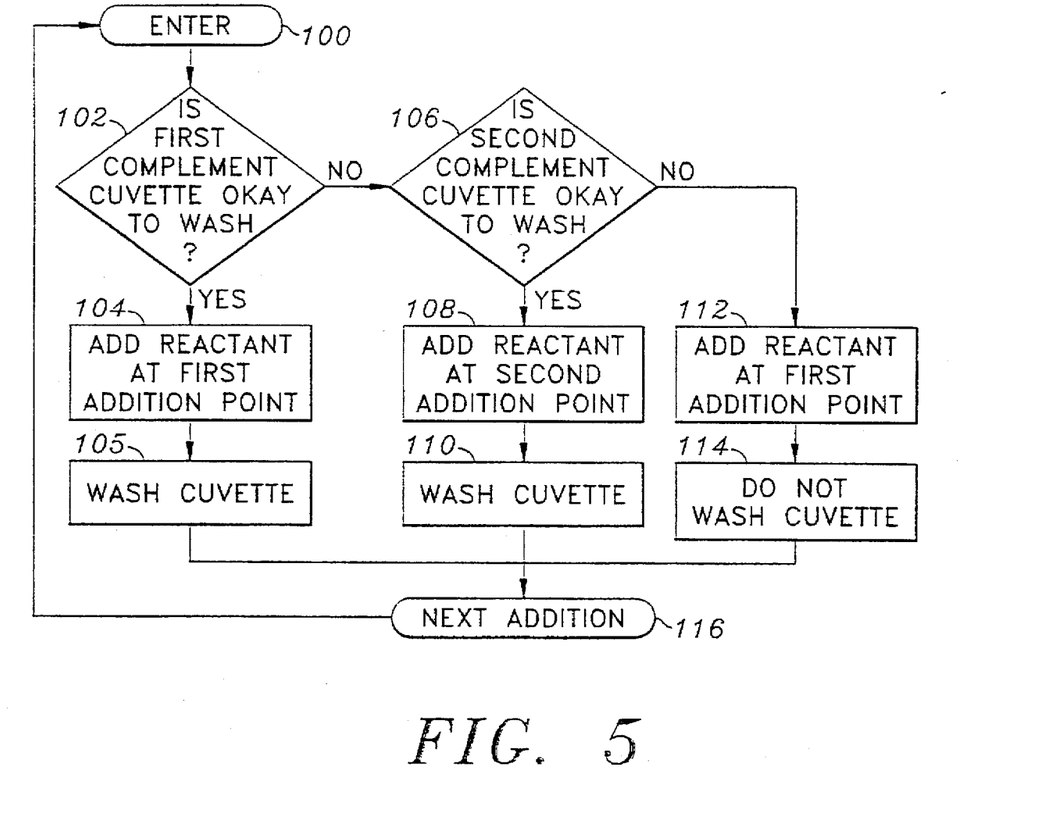
FIG. 5 is a logic flow diagram illustrating the selection of cuvettes for opportunistic washing.

With reference to FIGS. 2 and 5, the cycle scheduling and sequence for improving throughput the analyzers will be described. During the cycling of the analyzer 10 the analysis carousel 22 is cycled between the spin cycles (where the reaction is analyzed by photometric technique) and park cycles where reactants and samples are added to cuvettes and cuvettes are washed. The processor identifies cuvettes 24 and adds reactant and samples to the cuvettes 24 according to the constructed worklist, As the reactions take place, they are analyzed during the aforementioned spin cycles. Upon completion of the reactions and any secondary addition and analysis, the processor identifies the inventory of reaction complete cuvettes 24 which are ready to be washed. Receiving the inventory of wash-ready cuvettes 24, the processor, according to the present invention, adds reactant to a designated other cuvette according to the steps shown in FIG. 5.

With reference to FIG. 5, when the worklist requires addition of reactant, the reactant addition sequence is initiated as at 100. At this point, the processor identifies cuvettes 24 which are available for reactant addition in comparison to the inventory of wash-ready cuvettes. Based upon this comparison, the processor determines whether to add reactant at either the first or second reactant addition points which will locate, during the same park cycle, a wash-ready cuvette at the wash point. Accordingly, the processor for each of the first and second reactant addition points determines a wash complement. Wash complements are those cuvettes 24 during a park cycle which would be positioned at the wash point if reactant were added during that same park cycle. The first wash complement is the cuvette located at the wash point 61 if reactant were added at the first reactant addition point 59a to a designated cuvette 24 and the second wash complement is the cuvette 24 located at the wash point 61 if reactant were added to the same cuvette parked at the second reactant addition point 59b. As can be appreciated, the first and second reactant addition points 59a, b define, for a cuvette designated to receive reactant, two wash-complement cuvettes 24.

If the first wash complement is in the inventory of wash-ready cuvettes as determined by step 102, the processor adds reactant at the first reactant addition point 59a as shown by step 104 and simultaneously washes the first wash complement as shown by sequence step 105. If the first wash complement is not in the inventory of wash-ready cuvettes, the processor determines at 106 whether the second wash complement is in the inventory of wash-ready cuvettes. If so, as shown by steps 108 and 110, the processor controls the analysis carousel 22 to park and locate the second wash complement at the wash point 61, to add reactant at the second reactant addition point 59b and wash the second wash complement.

If neither of the first or second wash complements are wash-ready, the cuvette 24 designated for reactant addition is parked during a park cycle and reactant is added at the first reactant addition point 59a as shown by step 112 and no washing occurs during this park cycle as shown by 114.

Thereafter, the processor identifies the next cuvette 24 at 116 to receive reactant and determine whether simultaneous washing can take place as described above.

Accordingly, by providing the alternate first and second reactant addition points 59a, b, the processor can select the addition point which results, if available from the inventory, positioning a wash-ready cuvette i.e., the first or second wash complement cuvette at the wash point 61 so that simultaneously washing and reactant addition can take place.

While the above description sets forth separate stations for addition of reactant and sample, it can be understood that these reaction components (samples and reactants) could as well be added to cuvettes 24 at a single product introduction station. For example, the reactant wheel 26 could be loaded with both samples and reactants and their identities and locations provided to the processor. The sample wheel 20 would be eliminated. The reactant transfer station 46 would become a component transfer station adapted to transfer samples and reactants to the cuvettes at component addition points 59a, b on the analysis carousel 22.

According to another embodiment of the present invention, the sample transfer station 30 may be also arranged like the reactant transfer station to alternatively deliver sample to one of a pair of cuvettes 24. In this fashion the processor can examine the sets of cuvettes to determine whether or not the addition of sample to a cuvette 24 designated to receive sample at one or the other of the sample addition points shown as 37a, b (FIG. 2), results in the positioning of a wash-ready cuvette at the wash station 60 so that opportunistic washing of a designated cuvette can take place during the park cycle at which sample is added to another cuvette.

By providing the first and second additional points, the throughput of the analyzer 10 can be increased without the addition of more wash stations, reactant or sample transfer stations. It is believed that providing an analyzer 10 according to the first embodiment of the present invention which includes the first and second reactant introduction points 59a, b (and a single sample addition point 37), can increase the throughput of the analyzer 10 by between 7-10%. This advantage is obtained without the addition of other stations on the analyzer 10.

While I have shown and described certain embodiments of the present invention it is to be understood that it is subject to many modifications and changes without departing from the spirit and scope of the claims herein.

What is claimed is:

1. An analyzer for assaying a plurality of samples comprising:
    (a) a rotatable carousel having a plurality of peripheral, re-useable cuvettes;
    (b) at least one reaction component station proximate to the carousel for selectively adding reaction components to either of two cuvettes parked on the carousel proximate to the component station, the component station being capable of adding a component to a cuvette at a first component addition point on the carousel or to a cuvette at a second component addition point on the carousel, the at least one reaction component station being further capable of placing into a single cuvette on the carousel a portion of one of the samples and an assay reactant, to bring about a reaction for assay, the reaction for assay being of the type which progresses over time from the onset of the reaction to the completion of the reaction;
    (c) a wash station proximate to the carousel for washing a used cuvette parked proximate to the wash station;
    (d) an analysis station for analyzing the progress of the assay in each cuvette as the cuvette passes the analysis station and identifying cuvettes in which the assay is complete and are wash-ready;
    (e) a drive for rotating the carousel to move the cuvettes from station to station and past the analysis station; and
    (f) a controller for (1) determining an inventory of wash-ready cuvettes, (2) designating a target cuvette suitable to accept a reactant, (3) determining first and second wash complements, wherein the first wash complement is the cuvette which would be positioned at the wash station when the target cuvette is positioned at the first addition point and the second wash complement is the cuvette which would be positioned at the wash station when the target cuvette is positioned at the second addition point, (4) comparing the wash complements to the inventory of wash-ready cuvettes to determine if one or both of the wash complements are wash-ready, (5) if the first wash complement is wash-ready, parking the target cuvette at the first addition point and operating the wash station and the reaction component station at the first addition point, so as to simultaneously wash the first wash complement and add reactant to the target cuvette, (6) if the first wash complement is not wash-ready, but the second wash complement is wash-ready, parking the target cuvette at the second addition point and operating the wash station and the reaction component station at the second addition point, so as to simultaneously wash the second wash complement and add reactant to the target cuvette, and (7) if both the first and second wash complements are not wash-ready, parking the target cuvette at the first addition point and operating the reaction component station, but not operating the wash station, so as to add reactant to the target cuvette.

2. The analyzer of claim 1 wherein the controller drives the carousel to spin the carousel for photometric reaction analysis for a first time period and indexes, and parks the carousel for a second time period seriatim.

3. The analyzer of claim 1 wherein the controller stores the status of each cuvette to determine cuvettes for component addition and for washing.

4. The analyzer of claim 3 further including an inventory of a selection of components disposed on a moveable platform, the controller adapted to index the platform to position selected components proximate the component station, said component station adapted to uptake components from the platform and to move to one of the first and second addition points for introduction of component to the designated cuvette.

5. The analyzer of claim 4 wherein the first and second component addition points are disposed to register with adjacent cuvette positions on the carousel.

6. The analyzer of claim 1 including controller means to control the drive of the carousel, to store the status of cuvettes as clean, in assay, or wash-ready and to control the parking of the cuvettes to position a wash-ready cuvette at the wash station and a clean cuvette at one of the first or second component addition points.

7. An analyzer for assaying a plurality of samples comprising:
    (a) a rotatable carousel having a plurality of peripheral, re-useable cuvettes;
    (b) a sample station proximate to the carousel for selectively adding a sample to a cuvette parked proximate to the sample station;
    (c) a reactant station proximate to the carousel for selectively adding a reactant to either of two cuvettes parked on the carousel proximate to the reactant station, the reaction station being capable of adding reactant to a cuvette at a first addition point on the carousel or to a second addition point on the carousel, the reactant being capable of reacting with a portion of one of the samples in a cuvette to bring about a reaction for assay the reaction for assay being of the type which progresses over time from the onset of the reaction to the completion of the reaction;

(d) a wash station proximate to the carousel for washing a used cuvette parked proximate to the wash station;

(e) an analysis station for analyzing the progress of the assay in each cuvette as the cuvette passes the analysis station and identifying cuvettes in which the assay is complete and are wash-ready;

(f) a drive for rotating the carousel to move the cuvettes from station to station and past the analysis station; and (g) a controller for (1) determining an inventory of wash-ready cuvettes, (2) designating a target cuvette suitable to accept a reactant, (3) determining first and second wash complements, wherein the first wash complement is the cuvette which would be positioned at the wash station when the target cuvette is positioned at the first addition point and the second wash complement is the cuvette which would be positioned at the wash station when the target cuvette is positioned at the second addition point, (4) comparing the wash complements to the inventory of wash-ready cuvettes to determine if one or both of the wash complements are wash-ready, (5) if the first wash complement is wash-ready, parking the target cuvette at the first addition point and operating the wash station and the reaction component station at the first addition point, so as to simultaneously wash the first wash complement and add reactant to the target cuvette, (6) if the first wash complement is not wash-ready, but the second wash complement is wash-ready, parking the target cuvette at the second addition point and operating the wash station and the reaction component station at the second addition point, so as to simultaneously wash the second wash complement and add reactant to the target cuvette, and (7) if both the first and second wash complements are not wash-ready, parking the target cuvette at the first addition point and operating the reaction component station, but not operating the wash station, so as to add reactant to the target cuvette.

8. The analyzer of claim 7 wherein the controller drives the carousel to spin the carousel for photometric reaction analysis for a first time period and indexes, and parks the carousel for a second time period seriatim.

9. The analyzer of claim 8 wherein the controller stores the status of each cuvette to determine cuvettes for reactant addition, sample addition and for washing.

10. The analyzer of claim 9 further including a reactant wheel adapted to retain a selection of reactants, the controller adapted to index the reactant wheel to position selected reactants proximate the reactant station, said reactant station adapted to uptake reactant from the reactant carousel and to pivot to traverse an arc to the first and second addition points for introduction of reactant to the designated cuvette.

11. The analyzer of claim 10 wherein the first and second reactant addition points are disposed to register with adjacent cuvette positions on the reactant carousel.

12. The analyzer of claim 7 wherein the sample station is adapted to add sample to one of a first or a second sample addition points, the controller parking the carousel so that a wash-ready cuvette is parked at the wash station and a cuvette to receive sample is positioned at one of the first or second sample addition points and operating the wash and sample stations together to wash the wash-ready cuvette and add sample to a cuvette at either the first or the second sample addition point.

13. An improved analyzer having a rotatable, circular reaction carousel including circumferentially spaced, re-useable, cuvettes each processed to be designated to receive a selected reactant and a selected sample for reaction and analysis and, post analysis, designated to be washed and re-used, and a drive to index the carousel to park cuvettes for receipt of reactant, sample and wash, and analysis, the improvement comprising:

a wash station operated to engage and wash a wash-ready cuvette parked thereat;

a reactant station operated to introduce a reactant to either of two cuvettes parked on the carousel at a first reactant addition point and at a second reactant addition point, respectively;

a sample station operated to engage and introduce a sample to a cuvette parked thereat;

a controller for (1) determining an inventory of wash-ready cuvettes, (2) designating a target cuvette suitable to accept a reactant, (3) determining first and second wash complements, wherein the first wash complement is the cuvette which would be positioned at the wash station when the target cuvette is positioned at the first addition point and the second wash complement is the cuvette which would be positioned at the wash station when the target cuvette is positioned at the second addition point, (4) comparing the wash complements to the inventory of wash-ready cuvettes to determine if one or both of the wash complements are wash-ready, (5) if the first wash complement is wash-ready, parking the target cuvette at the first addition point and operating the wash station and the reaction component station at the first addition point, so as to simultaneously wash the first wash complement and add reactant to the target cuvette, (6) if the first wash complement is not wash-ready, but the second wash complement is wash-ready, parking the target cuvette at the second addition point and operating the wash station and the reaction component station at the second addition point, so as to simultaneously wash the second wash complement and add reactant to the target cuvette, and (7) if both the first and second wash complements are not wash-ready, parking the target cuvette at the first addition point and operating the reaction component station, but not operating the wash station, so as to add reactant to the target cuvette, so that the controller controls the drive and operation of the stations to process cuvettes and index the carousel to spin the carousel for photometric analysis for a first time period and index, positions and parks cuvettes at the stations for a second time period seriatim such that a wash-ready cuvette is parked at the wash station and a selected cuvette is, during the same park time period, parked at one of the first or second reactant addition points, and so that the controller operates the stations to wash the wash-ready cuvette while reactant is added to the selected cuvette at one of the addition points.

14. The improved analyzer of claim 13 further wherein the sample station is operated to add sample to cuvettes at either of a first or second sample addition point, the controller controlling the drive and indexing of the carousel to park a wash-ready cuvette at the wash station and a cuvette to receive sample at one of the first or second sample addition points and to control the stations to wash the wash-ready cuvette and add sample during the same park period.

* * * * *